(12) United States Patent
Pitkänen et al.

(10) Patent No.: US 9,506,884 B2
(45) Date of Patent: Nov. 29, 2016

(54) PLANAR SENSOR AND ITS MANUFACTURING METHOD

(75) Inventors: Temmo Pitkänen, Espoo (FI); Juha Lindström, Espoo (FI)

(73) Assignee: ELSI TECHNOLOGIES OY, Vantaa (FI)

( * ) Notice: Subject to any disclaimer, the term of this patent is extended or adjusted under 35 U.S.C. 154(b) by 152 days.

(21) Appl. No.: 14/239,453

(22) PCT Filed: Sep. 4, 2012

(86) PCT No.: PCT/FI2012/050854
§ 371 (c)(1),
(2), (4) Date: Apr. 15, 2014

(87) PCT Pub. No.: WO2013/034802
PCT Pub. Date: Mar. 14, 2013

(65) Prior Publication Data
US 2015/0077142 A1   Mar. 19, 2015

(30) Foreign Application Priority Data

Sep. 5, 2011   (FI) ..................... 20115869

(51) Int. Cl.
*G01R 27/32* (2006.01)
*G01N 27/04* (2006.01)
(Continued)

(52) U.S. Cl.
CPC ............ *G01N 27/041* (2013.01); *B32B 37/02* (2013.01); *B32B 37/18* (2013.01); *G01B 7/003* (2013.01); *G01B 7/14* (2013.01); *G01D 5/2405* (2013.01); *H03K 17/9622* (2013.01); *B32B 2307/51* (2013.01); *B32B 2457/08* (2013.01); *B32B 2471/00* (2013.01); *G01R 29/14* (2013.01); *G01V 3/02* (2013.01); *G08B 13/10* (2013.01); *H03K 2017/9602* (2013.01);
(Continued)

(58) Field of Classification Search
CPC ...... G01N 24/41; G01N 27/02; G01N 27/06; A61B 5/0537; A61B 5/4872
See application file for complete search history.

(56) References Cited

U.S. PATENT DOCUMENTS 4,429,301 A * 1/1984 Crumley ................ H03M 11/24
340/14.1
6,515,586 B1   2/2003 Wymore
(Continued)

FOREIGN PATENT DOCUMENTS

| JP | 2002-140771 A | 5/2002 |
|---|---|---|
| WO | WO 2008/068387 A1 | 6/2008 |
| WO | WO 2010/131963 A1 | 11/2010 |

*Primary Examiner* — Tung X Nguyen
*Assistant Examiner* — Dominic Hawkins
(74) *Attorney, Agent, or Firm* — Birch, Stewart, Kolasch & Birch, LLP (57) ABSTRACT

A planar sensor having a conductor pattern for electric field sensing and its manufacturing method, the planar sensor comprising arrays of planar electrically conductive sensor areas (2) arranged to follow each other in a successive manner along the longitudinal direction, and conductors connecting electrically conductive sensor area to at least one connector, wherein the sensor further comprises a first elastic flooring layer (3) and at least one of the following: a second elastic flooring layer (4) or a flexible circuit board, and the electrically conductive sensor areas (2) and the conductors are attached between the first elastic flooring layer (3) and the second elastic flooring layer (4) or between the first elastic flooring layer (3) and the flexible circuit board to form a unitary floor sensor structure.

8 Claims, 7 Drawing Sheets

(51) Int. Cl.
  *G01D 5/24* (2006.01)
  *H03K 17/96* (2006.01)
  *B32B 37/02* (2006.01)
  *B32B 37/18* (2006.01)
  *G01B 7/00* (2006.01)
  *G01B 7/14* (2006.01)
  *G08B 13/10* (2006.01)
  *G01R 29/14* (2006.01)
  *G01V 3/02* (2006.01)
  *H05K 3/28* (2006.01)
  *H05K 1/11* (2006.01)

(52) U.S. Cl.
  CPC .............. *H03K 2217/96015* (2013.01); *H03K 2217/960755* (2013.01); *H05K 1/118* (2013.01); *H05K 3/281* (2013.01); *H05K 2203/1545* (2013.01); *Y10T 156/1089* (2015.01)

(56) References Cited

U.S. PATENT DOCUMENTS

| | | | |
|---|---|---|---|
| 2005/0092519 A1* | 5/2005 | Beauchamp | H05K 3/4691 174/255 |
| 2006/0171570 A1 | 8/2006 | Brendley et al. | |
| 2007/0181424 A1* | 8/2007 | Frey | G01N 27/3276 204/403.01 |
| 2008/0104735 A1* | 5/2008 | Howland | F41H 1/02 2/2.5 |
| 2010/0021683 A1* | 1/2010 | Junghans | H05B 3/34 428/116 |
| 2010/0305427 A1* | 12/2010 | Huber | A61B 19/5244 600/424 |
| 2011/0174878 A1* | 7/2011 | Ropponen | H01Q 1/22 235/439 |

* cited by examiner

PLANAR SENSOR AND ITS MANUFACTURING METHOD

FIELD OF INVENTION

This invention relates to planar sensors and their manufacturing methods. Especially the present invention relates to a planar sensor operating as a floor sensor and having a conductor pattern for electric field sensing and its manufacturing method.

BACKGROUND

Near Field Imaging is used to monitor, for example, human movement in room facilities. Near Field Imaging systems are used in floor mounted planar sensors, whereby information is retrieved about the persons' location and condition by measuring the change in impedance caused by a conductive object, e.g. a human. Such arrangement can be applied in many applications, for instance senior homes etc. to observe senior citizens, or airports for monitoring movement of the passengers.

One such Near Field Imaging related planar sensing system which is specifically suitable for senior citizens home monitoring is presented in WO2005020171. Such a system can be used to monitor vital signs of, among other things, a nursing home resident that has fallen. The floor sensor transmits the position, respiratory rate and pulse of the resident to a nurse room monitor. The most central component of the system is a sensor covering the entire apartment floor. The sensor is installed under the floor covering. The sensor has a printed pattern which is made of metal or graphite dye. This kind of sensor can be installed under conventional floor coating structures like parquet or plastic mat.

Further, WO2006003245 and WO2008068387 disclose sensor structures where the sensors are web-like and consist of several sequential electrically conducting areas in the same plane. Tracking of the object on the sensor, like a human, is based on the capacitance change between adjacent electrically conducting areas in the same plane.

Electrically conducting areas are typically metal, and they can be formed on a flexible circuit board acting as a substrate, for example, as printed layers, laminate layers, etched layers, or as foils. The metal is typically aluminium or copper and the conducting areas are connected to the system controlling electronic control unit next to the sensor by each with their own connecting wire, as is presented in WO2008068387A1.

A problem with the prior art floor sensor systems is that the sensor is installed separately from the flooring, ie. first the sensor is installed on the floor and after that the flooring is installed on the sensor. The separate installation of the sensor and the flooring is time consuming and complex. A further problem with the prior art sensor systems is the complex contact arrangement between the sensor conductors and the connection cable.

SUMMARY OF THE INVENTION

The purpose of this invention is to achieve an entirely new kind of a planar sensor operating as a floor sensor and a method of manufacturing it.

The basic idea of the present invention is to integrate the planar sensor and the flooring into a unitary floor sensor structure and to manufacture this unitary structure in a continuous process. In the present invention the conductive sensor areas and the conductors and the flooring are attached together.

The present invention makes is possible to install the sensor as a unitary integrated sensor-flooring-unit which makes the installation very simple. Further, due to the peeling areas also the electrical installation between the sensor conductors and the connection cable is easy.

In a preferred embodiment of the present invention the flooring layer is provided with peeling areas or stripes.

In a preferred embodiment of the present invention the conductive sensor areas and the conductors are embedded inside the flooring between different flooring layers. In this way the sensor areas and conductors can be well protected against mechanical damage during the installation and use.

In a preferred embodiment of the present invention a protective film is used between a flooring layer and the conductive areas and conductors.

In a preferred embodiment of the present invention the conductive areas and the conductors are arranged on an elastic circuit board.

In a preferred embodiment of the present invention the flooring layers and the conductive areas and conductor layers are laminated together in a continuous roll-to-roll process.

In a preferred embodiment of the present invention the floor sensor is manufactured in a continuous extrusion process.

The present invention is in detail defined in enclosed independent claims relating to a planar sensor and its manufacturing method, and its preferred embodiments are described in dependent claims.

In a preferred embodiment the conductive wires such as copper wires of the sensor mat, which are often etched to the sensor circuit board, are replaced by conducting material, e.g. carbon paint. In this way the manufacturing process becomes easier and the conductors could be applied for example by painting directly on the bottom surface of an upper flooring layer when the flooring consists of separate layers. In this embodiment no sensor circuit board is thus needed.

Furthermore, the sensor structure presented here can also be characterized by the feature that the integrated sensor structure can be cut across the longitudinal direction of the web anywhere along this direction, and the cutoff sensor laminate will form a functional entity up to the sensor count that does not exceed the number of conductors crossing the cutting edges. Thus, during manufacturing, the structure of the sensor web is insensitive to the number of the conductive areas which are required in a specific sensor web for a given application or system to be assembled.

The integrated sensor structure is preferably in a web form. The flooring having a thickness of typically 1 to 10 mm and even more is composed of plastic floor covering material or a combination of such materials The flooring may thus have several layers, and the layers may be made of different materials. The flooring is flexible in order to conform with other surfaces on which it is placed. Besides one layer structure, the flooring may thus comprise more layers attached to each other.

The electrically conductive areas comprise electrically conductive material, and the electrically conductive areas can be, for example, but are not limited to, printed layers, coated layers, evaporated layers, electrodeposited layers, sputtered layers, laminated foils, etched layers, foils or fibrous layers. The electrically conductive area may comprise conductive carbon, metallic layers, metallic particles, or fibers, or electrically conductive polymers, such as polyacetylene, polyaniline, or polypyrrole. Metals that are used for forming the electrically conductive areas include for example aluminum, copper and silver. Electrically conductive carbon may be mixed in a medium in order to manufacture an ink or a coating. The same electrically conductive materials also apply to the conductors. Suitable techniques for forming the electrically conductive areas include, for example, etching or screen printing (flat bed or rotation), gravure, offset, flexography, inkjet printing, electrostatography, electroplating, and chemical plating.

Each electrically conductive area to be used for sensing is connected to a conductor which forms an electrically conductive path between the electrically conductive areas and the output. The conductors may form a group of parallel conductors which each of them is adapted to join. When one conductor joins the group, each of the other conductors of the group gives space for the joining conductor so that the conductors do not cross each other. The group of conductors advance in the longitudinal direction of the substrate.

The above-mentioned principle as far as the conducting area and conductor patterns can be implemented in different ways, as is described in WO2008068387.

The sensor web comprises repetitive patterns which comprise successive and/or sequential conductive areas and their conductors. For example, one pattern may be formed from five successive conductive areas and their conductors. The above-mentioned pattern is repetitive over the length of the web.

The number of successive electrically conductive areas 1 to N in the web is defined by the total number of conductor lines arranged to run along the web direction. Typically, the number of conductors is kept constant along the web, which means that when a new conductor is adapted to join the group of successive conductors and the other conductors in this group are adapted to give space for this joining conductor, then the run of the outermost conductor on the other side of this group is terminated. Thus, the total repetitive pattern of the successive conductive areas is defined by the total number of parallel conductor lines. This number can be freely chosen according to a given application.

BRIEF DESCRIPTION OF THE FIGURES

In the following, the invention will be described in more detail with reference to the enclosed drawings, in which.

DETAILED DESCRIPTION OF PREFERRED EMBODIMENTS

The present invention is based on an idea to integrate a planar sensor and a flooring into a unitary floor sensor structure and to manufacture this unitary structure in a continuous manufacturing process. The planar sensor is thin and has a thickness 10-100 µm whereby the flooring is essentially thicker and has a thickness 1-10 mm. Further, the flooring layer is provided with peeling areas or peeling stripes.

Figure 1A:
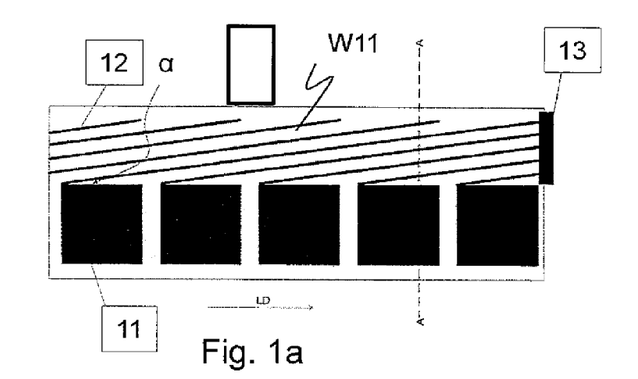
FIGS. 1a, 1b, 2a, 2b, 3a, 3b, 4a and 4b show the top views of sensors for monitoring conductive objects.
Figure 1B:
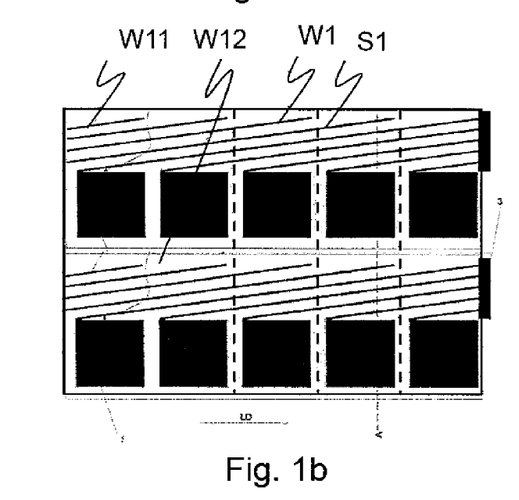

FIG. 1b illustrates a floor sensor W1 for monitoring electrically conductive objects, for example the movement and location of a human on a floor. The sensor web W1 comprises several, in FIG. 1b two, identical parallel sensor web units W11, W12 having successive electrically conductive areas 11 according to FIG. 1a. A conductor 12 connects the electrically conductive area 11 to an output 13. The output 13 is provided with a connector. The parallel conductors 12 extend linearly and form an angle α to the longitudinal direction LD of the web.

The sensor web W1 is further provided with transversal peeling areas or peeling stripes S1 having a f.ex. width 10 to 100 mm. Peeling areas or peeling stripes S1 could be located on or both sides of the sensor film between the conductive areas. In these areas the uppermost flooring surface is not attached to the elastic circuit board or another flooring layer lying under it and can easily be peeled off to make the electrical connection between the sensor and the connection cables easier.

Figure 2A:
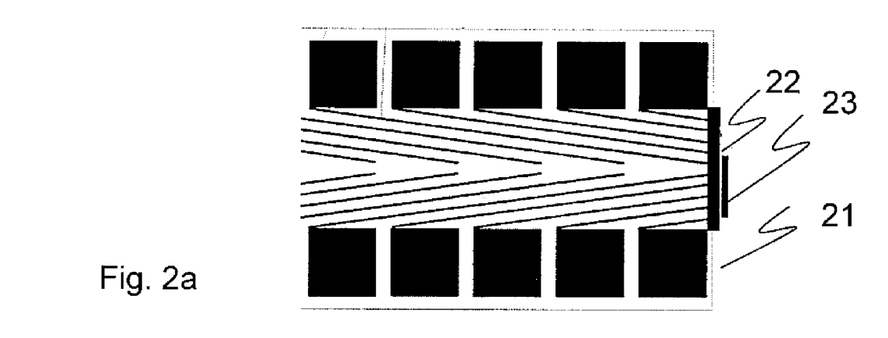
Figure 2B:
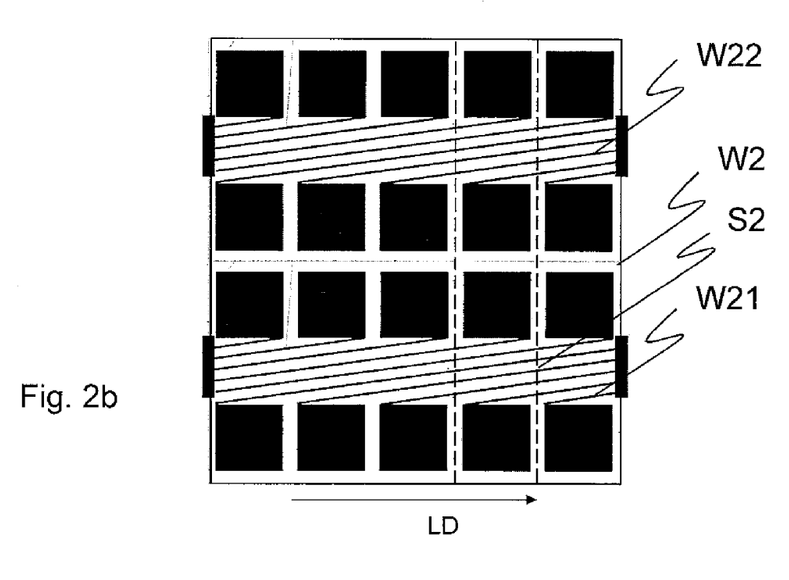

FIG. 2b shows another possible lay-out of a sensor web. The sensor web W2 comprises identical parallel sensor web units W21, W22 having successive electrically conductive areas 21 according to FIG. 2a. Conductors 22, which connect the electrically conductive areas 21 on the upper row to an output 23 on the left hand side, are parallel to conductors 23, which connect the electrically conductive areas 21 on the lower row to an output 23 on the right hand side. The parallel conductors 22 extend linearly and form an angle to the longitudinal direction LD of the web W. The sensor further comprises peeling areas S2.

Figure 3A:
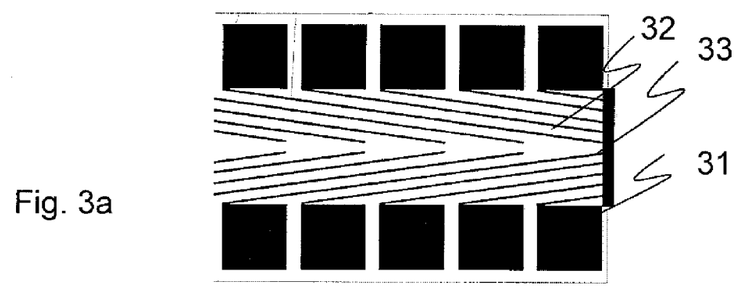
Figure 3B:
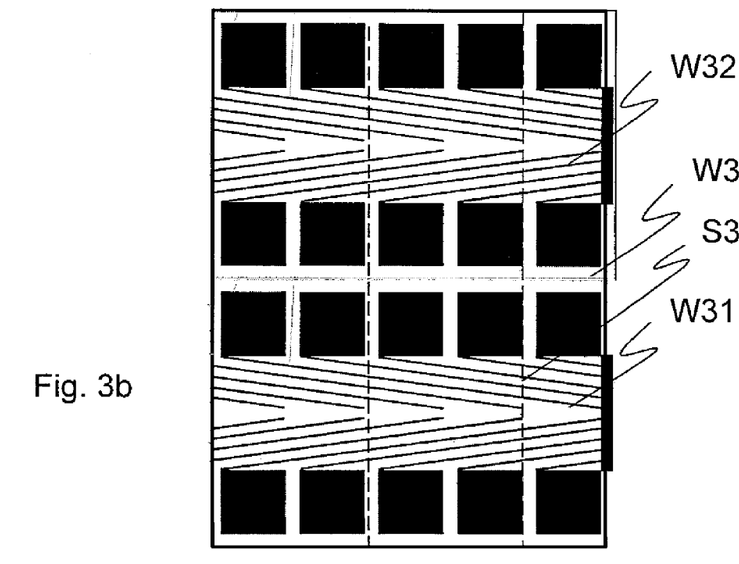

FIG. 3b shows yet another possible lay-out of a sensor web. The sensor web W3 comprises identical parallel sensor web units W31, W32 having successive electrically conductive areas 31 according to FIG. 3a. The web comprises two rows of successive electrically conductive areas 31 and conductors 32 which connect the electrically conductive areas to an output 33. The electrically conductive areas 31 on the upper row and their conductors 32 and the electrically conductive areas 31 on the lower row and their conductors 32 form a mirror image. The conductors of the upper row are parallel to each other and so are the conductors of the lower row. The sensor further comprises peeling areas S3.

Figure 4A:
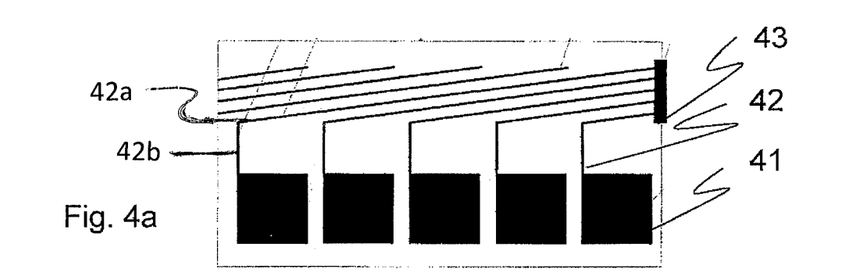
Figure 4B:
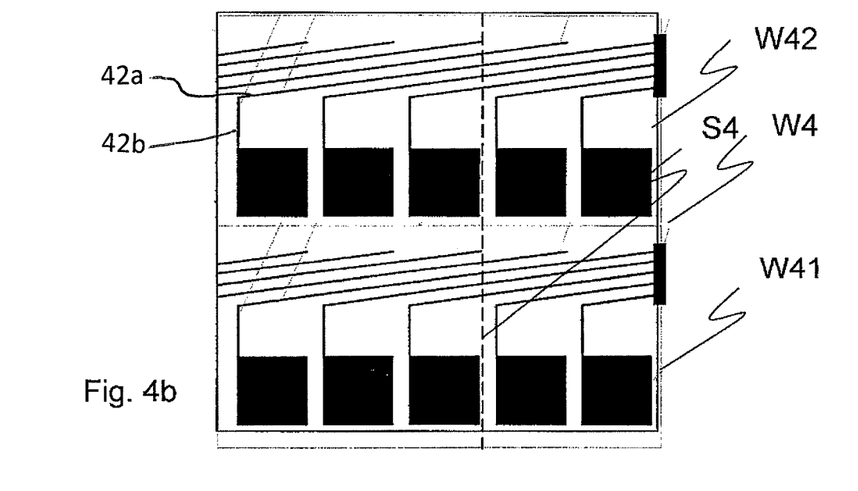

FIG. 4b further shows one possible lay-out of the sensor web. The sensor web W4 comprises identical parallel sensor web units W41, W42 having successive electrically conductive areas 41 according to FIG. 4a. Conductors 42 comprise first parts 42a which extend linearly, and they form an angle with the longitudinal direction LD of the web W. The conductors 42 may comprise second parts 42b which are transverse to the longitudinal direction of the sensor web. However, the shape of the second part may vary. The sensor further comprises peeling areas S4.

Figure 5A:
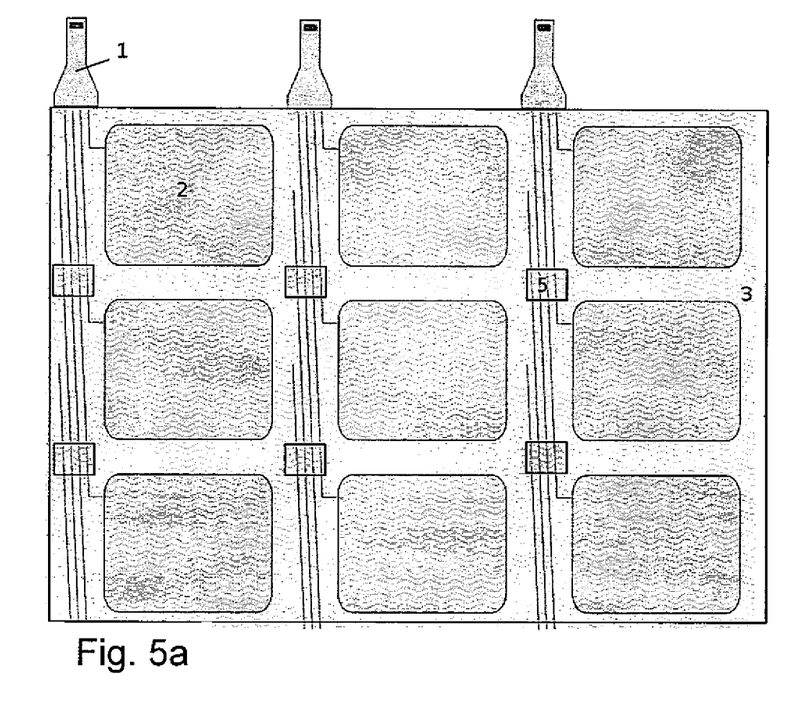
FIGS. 5a and 5b show sensor web and its cross-sectional view.
Figure 5B:
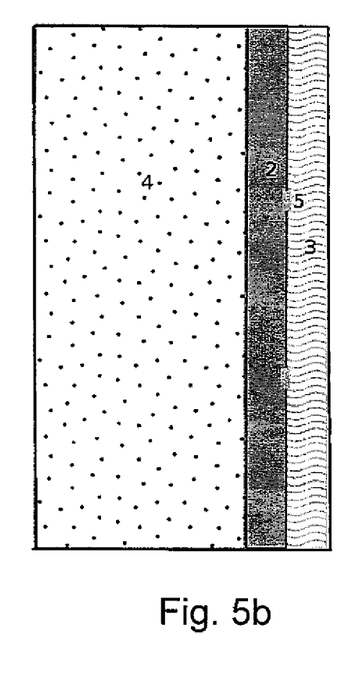

FIGS. 5a and 5b show sensor web and its cross-sectional view. A typical heterogeneous vinyl carpet consists of two layers 3 and 4. At the top there is a relatively thin wear layer 3 (e.g. 0.65 mm) and at the bottom there is a thicker foam layer providing sound reduction and shock absorbency. The idea is to embed the conductive layer 2 of the sensor forming the conductive areas and conductors between these carpet layers. One way to do this is to laminate the sensor PET foil 2 to the wear layer before the extrusion of the foam. Other possibilities include printing and other additive methods, where the conductive layer is built directly on the wear layer without any substrate. If there is a problem with getting the layers to bond to each other, one can add lots of holes to the conductive layer before the sensitivity decreases significantly.

One problem that must be solved is how to make a reliable connection to the conductive layer, when it is embedded inside the carpet. One way to do this is to add a peeling area 5 to those points of the sensor structure on the uppermost layer 3 where a connection is needed and then attaching a flex cable there with anisotropic adhesive.

Figure 6A:
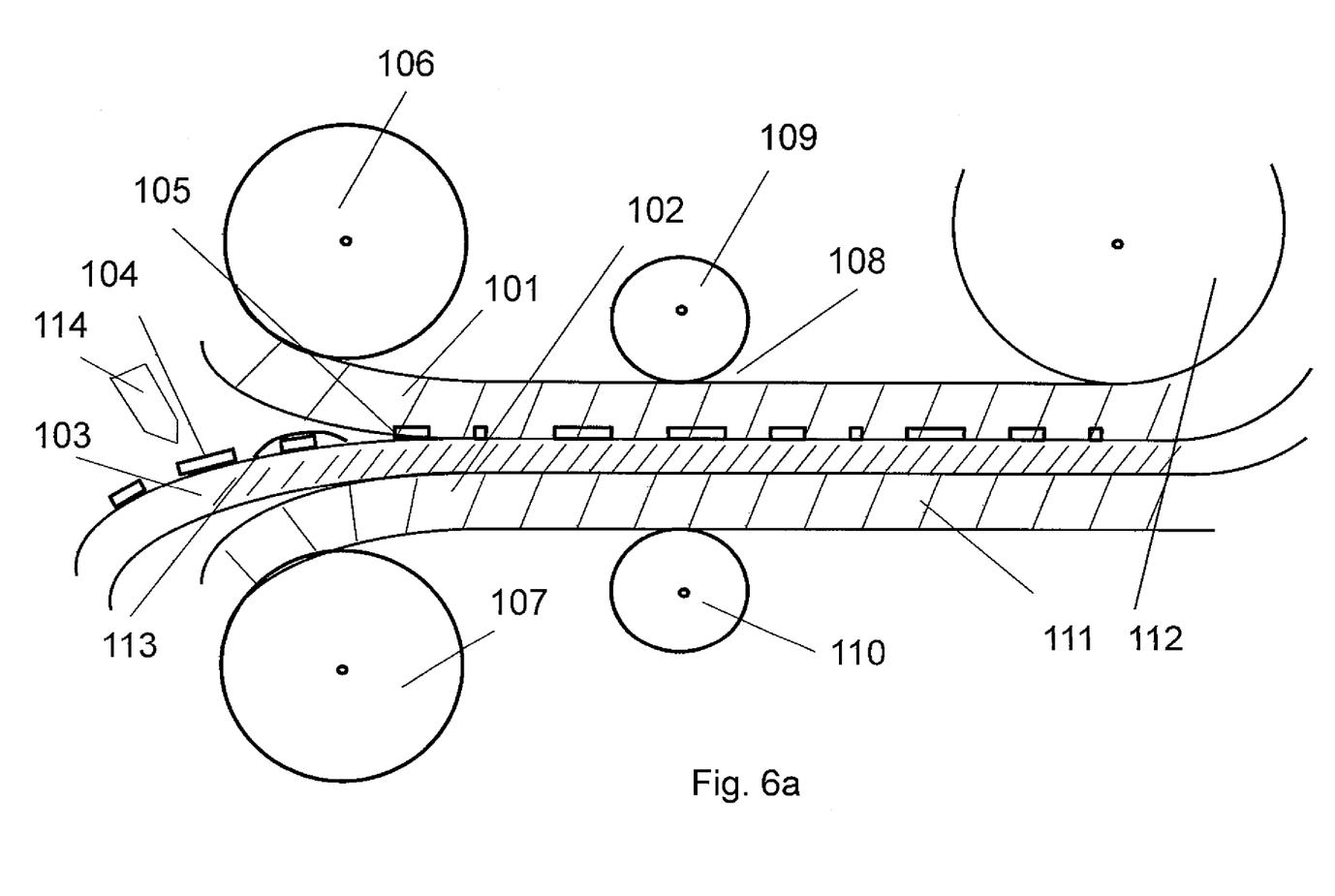
FIGS. 6a and 6b show schematic views of two manufacturing methods.

FIG. 6a presents a continuous roll-to-roll laminating process for manufacturing a floor sensor according to the present invention. FIG. 6a shows a cross section along a longitudinal line at the edges of the conductive areas and conductors. In FIG. 6a the flooring consists of two vinyl flooring layers, an upper layer 101 and a bottom layer 102 (a total thickness e.g. 5 mm, the layers may be similar or different), a thin elastic plastic circuit board 103 with the conductive areas 104 and conductors 105 on it. The thickness of the conductive areas, conductive layers and the conductors is totally e.g. 50 µm.

The circuit board has the same area as the flooring layers and is laminated between them. The circuit board, the conductive areas and the conductors may be protected by a thin plastic protective layer (not shown). The flooring layers 101 and 102 are both released from a release roll 106, 107 to a laminating nip 108 together with the circuit board with the conductive areas and the conductors whereby all the layers are laminated together with heat, pressure, and adhesives applied on the flooring layer surfaces facing each other and the circuit board.

The laminating nip is formed between two heated laminating rolls 109 and 110. All the layers are laminated together in the nip, and the laminated floor sensor web 111 is finally wound onto a third roll 112. The transversal peeling areas 113 are formed by applying a stripe of non-adhesive substance between the conductive areas from a nozzle 114 onto the circuit board 103 before the laminating nip. This non-adhesive substance prevents the lamination of the upper flooring layer and the circuit board and the conductors and makes it possible to peel the upper flooring layer so that to make a contact between the conductors and the external connection cables becomes easier.

It is also possible to laminate only one flooring layer in a similar way. In that case thus only one (uppermost) flooring layer is laminated together with the circuit board with the same area, the conductive areas and the conductors.

Figure 6B:
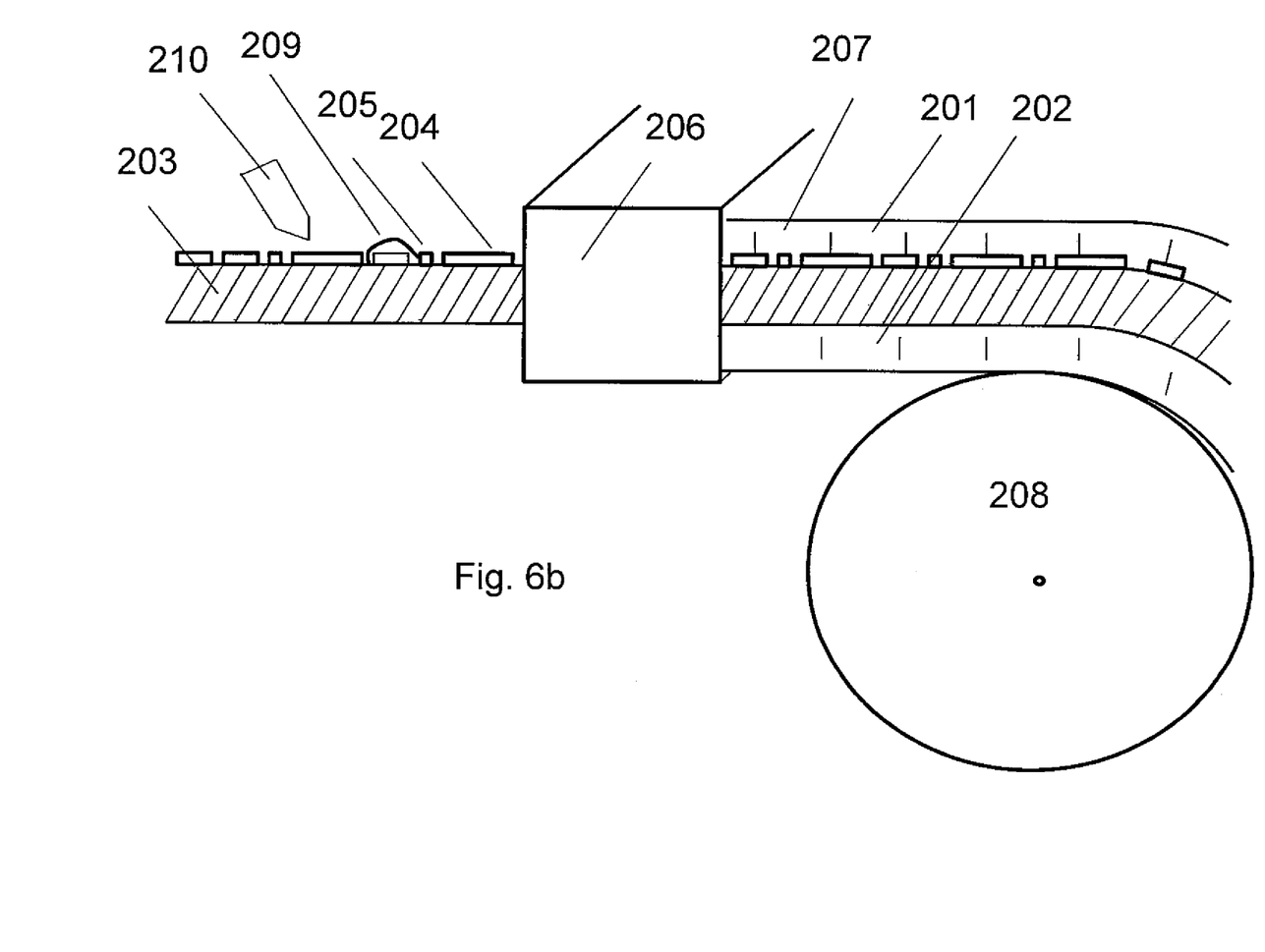

FIG. 6b presents correspondingly a continuous extrusion process for manufacturing a floor sensor according to the present invention.

Also in FIG. 6b the flooring in the final sensor structure consists of two flooring layers, an upper layer 201 and bottom layer 202 having the same thickness and structure as above. The material of the layers is extrudable plastic material that is suited for floorings. The sensor further comprises a thin elastic plastic circuit board 203 with the conductive areas 204 and conductors 205 on it. The thickness of the conductive areas, conductive layers and the conductors is totally e.g. 50 µm.

In the process the circuit board 203 with the conductive areas 204 and conductors 205 is conveyed to an extruder 206. In the extruder 206 the flooring material is extruded on both sides of the circuit board 203, and after that the sensor structure 207 is rolled on a roll 208. The transversal peeling areas 209 are formed by applying a stripe of non-adhesive substance between the conductive areas from a nozzle 210 onto the circuit board before extrusion.

The extrusion may be implemented on only one (upper) circuit board surface. Further, the process may be implemented in two sequences, first the lower flooring layer is extruded on the bottom of the circuit board, and after that the upper layer is extruded on the top of the circuit board.

In both processes the upper and lower flooring layers may consist of different materials.

It is also possible that the circuit board 203 and the conductive areas 204 and the conductors 205 would be first laminated together with the upper floor material 201, and then this entity is fed to the extruder which would extrude the bottom floor layer 202.

Throughout this application, the term "successive" is used when describing the mutual positioning of the sensor areas within an array consisting of such sensor areas. These arrays again will follow each other in a repetitive manner along the longitudinal direction of the web. Successive sensor areas are not limited here to embodiments where such areas follow each other along the longitudinal direction so that the area of the previous sensor needs to end in the longitudinal direction before the area of the successive sensor begins. It is also possible that these two or more sensor areas "overlap" each other in the cross web direction so that both sensors run side-by-side for a certain length of the web. All embodiments that are arranged to have galvanically separated sensor areas provided along the longitudinal direction of the web in some manner where this patterning advances along said longitudinal direction, are possible. The sensor areas within an array do not need to form any specific sequence.

A skilled person will readily understand that all the features of the sensor web are interchangeable. If a certain feature is explained in connection with a certain sensor web, it is clear that the feature can be replaced by such a feature which is explained in connection with another sensor web.

The invention claimed is:

1. A planar sensor having a conductor pattern for electric field sensing, comprising:
   arrays of planar electrically conductive sensor areas (11) arranged to follow each other in a successive manner along a longitudinal direction (LD), and
   conductors (12) for individually connecting electrically conductive sensor areas to at least one connector (13), said planar sensor further comprises a first elastic flooring layer (16) and at least one of the following: a second elastic flooring layer or a flexible circuit board, and
   a plurality of peeling areas or stripes positioned on selective areas of the planar sensor, said plurality of peeling areas or stripes being individually selectively connected between selective conductive sensor areas and to said at least one connector (13),
   the electrically conductive sensor areas (11) and the conductors (12) are attached between the first elastic flooring layer and the second elastic flooring layer or between the first elastic flooring layer and the flexible circuit board to form a unitary floor sensor structure.

2. The planar sensor according to claim 1, wherein the sensor comprises a first upper elastic flooring layer, a second elastic flooring layer and a flexible circuit board between the flooring layers on which circuit board the planar electrically conductive sensor areas (11) and the conductors are formed.

3. The planar sensor according to claim 2, wherein the thickness of the flooring layers is above 1 mm, and the thickness of the flexible circuit board and the electrically conductive sensor areas (11) and the conductors (12) is essentially less, and preferably in the range 10-100 µm.

4. The planar sensor according to claim 2, wherein at least the uppermost flooring layer is provided with at least transversal peeling areas or stripes (S1) arranged between the conductive areas.

5. The planar sensor according to claim 1, wherein the thickness of the flooring layers is above 1 mm, and the thickness of the flexible circuit board and the electrically conductive sensor areas (11) and the conductors (12) is essentially less, and preferably in the range 10-100 μm.

6. The planar sensor according to claim 1, wherein at least the uppermost flooring layer is provided with at least transversal peeling areas or stripes (S1) arranged between the conductive areas.

7. The planar sensor according to claim 6, wherein flooring layer in the peeling areas or stripes (S1) arranged between the conductive areas has an essentially weaker attachment to the layer under it.

8. The planar sensor according to claim 1, wherein a protective film is arranged between at least one flooring layer and the elastic circuit board.

* * * * *